(12) United States Patent
Müller et al.

(10) Patent No.: US 7,229,807 B2
(45) Date of Patent: Jun. 12, 2007

(54) DECOMPOSITION AND MODIFICATION OF SILICATE AND SILICONE BY SILASE AND USE OF THE REVERSIBLE ENZYME

(75) Inventors: Werner E. G. Müller, Wiesbaden (DE); Heinz Schröder, Wiesbaden (DE); Anatoli Krasko, Mainz (DE)

(73) Assignee: Biotechmarin GmbH, Mainz (DE)

( * ) Notice: Subject to any disclaimer, the term of this patent is extended or adjusted under 35 U.S.C. 154(b) by 0 days.

(21) Appl. No.: 10/530,240

(22) PCT Filed: Oct. 2, 2003

(86) PCT No.: PCT/EP03/10983

§ 371 (c)(1),
(2), (4) Date: Jul. 27, 2005

(87) PCT Pub. No.: WO2004/033679

PCT Pub. Date: Apr. 22, 2004

(65) Prior Publication Data

US 2006/0029939 A1 Feb. 9, 2006

(30) Foreign Application Priority Data

Oct. 3, 2002 (DE) ................ 102 46 186

(51) Int. Cl.
*C12P 3/00* (2006.01)
*C12P 9/00* (2006.01)
*C07H 21/04* (2006.01)
*C12N 9/16* (2006.01)

(52) U.S. Cl. .............. 435/168; 435/131; 435/196; 435/69.1; 435/252.3; 435/320.1

(58) Field of Classification Search .............. 435/6, 435/195; 536/23.2
See application file for complete search history.

(56) References Cited

FOREIGN PATENT DOCUMENTS

WO      WO 00/35993 A     6/2000

OTHER PUBLICATIONS

Schroder et al. ( pro mol. sub cellu biol. 2003 33, 249-268.*
Brawer, A. E. "Silicon and Matrix Macromolecules: New Research Opportunities of Old Diseases from Analysis of Potential Mechanisms of Breast Implant Toxicity" *Medical Hypotheses*, Jul. 1998, pp. 27-35, Vol. 51, No. 1.
Budavari, S. *The Merck Index, Twelfth Edition*, 1996, pp. 1459, Merck, Whitehouse Station.
Cha, J. N. et al. "Silicatein Filaments and Subunits From a Marine Sponge Direct the Polymerization of Silica and Silicones In Vitro," *Proceedings of the National Academy of Sciences of USA*, Jan. 1999, pp. 361-365, Vol. 96.
Krasko "Expression of Silicatein and Collagen Genes in the Marine Sponge Suberites Domuncula is Controlled by Silicate and Myotrophin," *European Journal of Biochemistry*, Aug. 2000, pp. 4878-4887, Vol. 267.
Schröder, H. C. et al. "Silicase, and Enzyme which Degrades Biogenous Amorphous Silica: Contribution to the Metabolism of Silica Deposition in the Demosponge Suberites Domuncula" *Progress in Molecular and Subcellular Biology*, 2003, pp. 249-268, vol. 33.
Shimuzu, K. et al. "Silicatein Alpha: L-Like Protein in Sponge Biosilica" *Proceedings of the National Academy of Sciences of USA*, May 1998, pp. 6234-6238, Vol. 95.
Venta, P. J. et al. "H.Sapiens Carbonic Anhydrase II (CAII) Gene, Exon 7, and Complete CDs" *EMBL 'Online!'*, Jan. 26, 1992, Database accession No. M77181, Abstract.

* cited by examiner

*Primary Examiner*—Rebecca E. Prouty
*Assistant Examiner*—Md Y. Meah
(74) *Attorney, Agent, or Firm*—Saliwanchik, Lloyd & Saliwanchik

(57) ABSTRACT

Silicatein is an enzyme of silicate-forming organisms used for the synthesis of their silicate scaffold. The present invention relates to the use of highly-expressed and highly active recombinant silicatein, silicatein isolated from natural sources after gene induction as well as silicatein-fusion proteins for the synthesis of amorphous silicon dioxide (silicic acids and silicates), siloxanes as well as modification of these compounds and their technical use.

4 Claims, 8 Drawing Sheets

Figure 1:
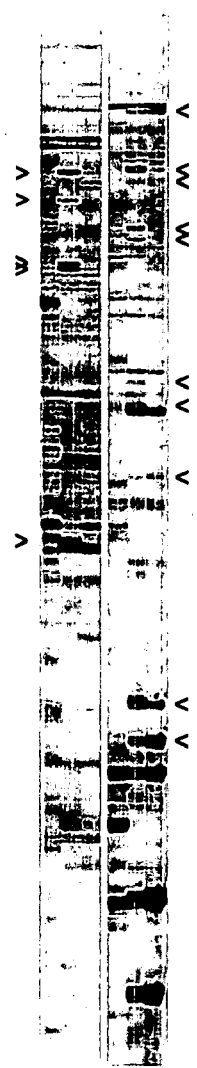

>carbo#SD long
MSAILKRNVPIQRVGLPLTSYVSRWASALPTRTHPFYKLVDDSTTPVT
RSTLLSAHMVDTLLDENQQSRHENQHTDTSYKMYQGLKFVVKTLFTPS
KCHRHFSTSAHLSAMGRHQSPINIITSSTTKGPSLKPLKFSKSWDKPV
IGTVKDTGYYLKFAPESAAEKCTLHTYNGEYILDHFHYHWGKKDGEGA
EHFIDGKQYDIEFHFVHKKVGLTDPDARDAFAVLGVFGKADPRLKING
IWELLSPSTVLTVDSTRNVADVVPSKLLPSARDYFHYEGSLTTPTYGE
VVHWFVLNEPIAVPSEYLSALRQMQADKEGTVIDSNYRELQEVHNRPV
QRFKSDEQGRGEFDDISKNEDIVEDLSKLSGNFIRELVRKIYW

FIG. 2A

```
GAATTCGGCACGAGGGACAACTTTGCATAACTTTTACTGTCCATGTTTAACGTTTAGATCTAG    63
TACTAGTAGTCTACAAGAACAACTGTCAACAACTGTCAGATTATGTGTATAAACCAAGATGTC   126
                                                          M  S      2
TGCAATTCTTAAGAGAAACGTACCTATCCAAAGAGTCGGTCTCCCACTGACCTCCTATGTCAG   189
  A  I  L  K  R  N  V  P  I  Q  R  V  G  L  P  L  T  S  Y  V  S    23
TAGATGGGCTTCTGCTCTGCCCACCAGGACCCATCCTTTTTACAAGTTGGTTGATGACAGTAC   252
  R  W  A  S  A  L  P  T  R  T  H  P  F  Y  K  L  V  D  D  S  T    44
CACCCCAGTGACAAGGTCTACTCTTCTCAGTGCTCATATGGTTGACACCTTGCTAGATGAGAA   315
  T  P  V  T  R  S  T  L  L  S  A  H  M  V  D  T  L  L  D  E  N    65
CCAGCAGAGCAGACATGAAAACCAACACACAGACACGTCTTACAAAATGTACCAGGGATTAAA   378
  Q  Q  S  R  H  E  N  Q  H  T  D  T  S  Y  K  M  Y  Q  G  L  K    86
ATTTGTTGTAAAGACGCTGTTTACTCCATCGAAATGCCACCGTCACTTCTCCACATCAGCTCA   441
  F  V  V  K  T  L  F  T  P  S  K  C  H  R  H  F  S  T  S  A  H   107
TTTGTCTGCCATGGGTCGACATCAATCCCCCATCAATATAATCACCTCCAGTACGACCAAAGG   504
  L  S  A  M  G  R  H  Q  S  P  I  N  I  I  T  S  S  T  T  K  G   128
ACCGTCATTGAAACCGTTAAAATTTAGCAAGAGTTGGGACAAGCCAGTAATCGGCACCGTCAA   567
  P  S  L  K  P  L  K  F  S  K  S  W  D  K  P  V  I  G  T  V  K   149
AGATACTGGCTATTATCTTAAATTTGCACCAGAATCTGCAGCAGAGAAGTGCACATTGCATAC   630
  D  T  G  Y  Y  L  K  F  A  P  E  S  A  A  E  K  C  T  L  H  T   170
GTACAATGGTGAATATATCCTAGATCATTTCCATTATCACTGGGGGAAGAAGGATGGGGAAGG   693
  Y  N  G  E  Y  I  L  D  H  F  H  Y  H  W  G  K  K  D  G  E  G   191
AGCAGAGCATTTCATCGATGGAAAACAATACGACATCGAGTTCCACTTTGTACATAAAAAGGT   756
  A  E  H  F  I  D  G  K  Q  Y  D  I  E  F  H  F  V  H  K  K  V   212
TGGGTTGACTGATCCAGATGCTAGAGACGCTTTTGCTGTTTTGGGCGTTTTTGGAAAGGCCGA   819
  G  L  T  D  P  D  A  R  D  A  F  A  V  L  G  V  F  G  K  A  D   233
CCCTCGTTTGAAGATCAATGGAATCTGGGAGCTACTCTCACCGTCAACTGTCCTGACTGTCGA   882
  P  R  L  K  I  N  G  I  W  E  L  L  S  P  S  T  V  L  T  V  D   254
CTCAACACGAAACGTCGCTGATGTTGTTCCCTCTAAGCTTCTCCCAAGTGCCAGAGACTATTT   945
  S  T  R  N  V  A  D  V  V  P  S  K  L  L  P  S  A  R  D  Y  F   275
TCACTATGAAGGTTCTTTGACCACACCTACGTATGGTGAGGTTGTGCACTGGTTTGTTCTCAA  1008
  H  Y  E  G  S  L  T  T  P  T  Y  G  E  V  V  H  W  F  V  L  N   296
TGAACCCATAGCTGTCCCTAGTGAGTATCTGTCAGCTCTGAGACAGATGCAAGCTGACAAAGA  1071
  E  P  I  A  V  P  S  E  Y  L  S  A  L  R  Q  M  Q  A  D  K  E   317
AGGTACTGTGATTGACTCAAACTATCGAGAGCTTCAAGAAGTCCACAATCGACCTGTGCAACG  1134
  G  T  V  I  D  S  N  Y  R  E  L  Q  E  V  H  N  R  P  V  Q  R   338
ATTTAAGAGTGATGAGCAAGGGAGAGGAGAATTTGACGATATTTCTAAGAATGAGGACATTGT  1197
  F  K  S  D  E  Q  G  R  G  E  F  D  D  I  S  K  N  E  D  I  V   359
GGAGGACTTGTCTAAATTGTCTGGTAACTTTATTAGAGAGCTGGTCAGGAAGATATATTGGTG  1260
  E  D  L  S  K  L  S  G  N  F  I  R  E  L  V  R  K  I  Y  W      379
ACCTTTTTCTACACTTGTTAGAGTTTTAGGCCAGAATACATTTCATCATTTGGACTGTTATTT  1323
TGTGTACACTGCTTAGCAGTTTATATAAACACTACAATGCCATTATTATAATATAGCCAATGC  1386
TGTGATTTGA                                                        1396
```

FIG. 2B

```
SIA_SUBDO   MSAILKRNVPIQRVGLPLTSYVSRWASALPTRHPFYKLVDDSTTPVTRSTLLSAHMVDTLLDENQQSRHENQHTDT   77
CAH2_HUMAN  ------------------------------------------------------------MSHH----------    4
             ~~~rec~~~

SIA_SUBDO   SYKMYQGLKFVVKTLFTPSKCHRHESTSAHLSAMGRHQSPINIITSSTTKGPSLKPLKFSKSWDKPVIGTVKDTGYY  154
CAH2_HUMAN  ----------------WGYGKHNGPEHWHKDFPIAK------GERQSPVDIDTHTAKYDPSLKPLSVSYDQATSLRILNNGHAEN   67
                            ⊢  e-CAdom~~~rec-s~~~              +++

SIA_SUBDO   LKEAPESAAEKCTLHTYNGEYIEDHFHYHWCKKDGEGAEHFIDGKQYDIEFHFVHKKVGLTDP----DARDAFAVLG  227
CAH2_HUMAN  VEEDDSQDKAVLKGGPLDCTYRLIQFHFHWGSLDGQGSEHTVDKKKYAAELHLVHWNTKYGDFGKAVQQPDGLAVLG  144
                                     N  N              ▲          ▲ ■ Z ■

SIA_SUBDO   VEGKADPRLKINGIWELLSPSTVLTVDSTRNVADVVPSKLLPSARDYEHYEGSLTTPTYGEVHWFVLNEPIAVPSE   304
CAH2_HUMAN  IFLKVG-SAKPGLQKVVDVLDSIKTKGKSADFTNFDPRGLLPESLDYWTYPGSLTTPPLLECVTWIVLKEPISVSSE  220
                                    ▲ ▲ ■        ▲                              +    ++

SIA_SUBDO   YISAIRQMQADKEGTVIDSNYRELQEVHNRPVQRFKSDEQGRGEEDDISKNEDIVEDLSKLSGNFIRELVRKIYW   379
CAH2_HUMAN  QVLKFRKLNFNGEG------EPEHMVDNWRPAQPLK-NRQIKASFK--------------------------------  260
                         e-CAdom +⊣                                 ~~~rec~~~
```

FIG. 3A

FIG. 6A
FIG. 6B
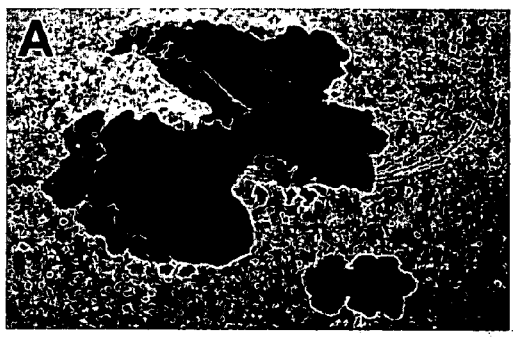
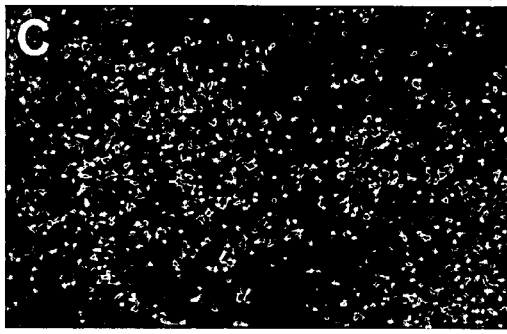
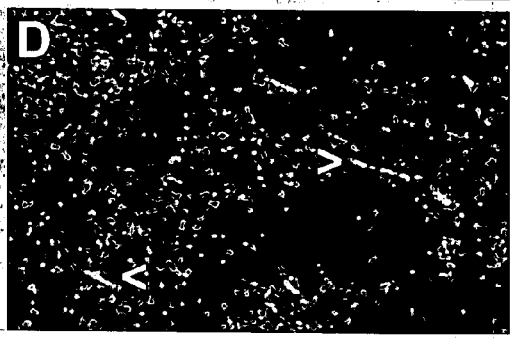
FIG. 6C
FIG. 6D
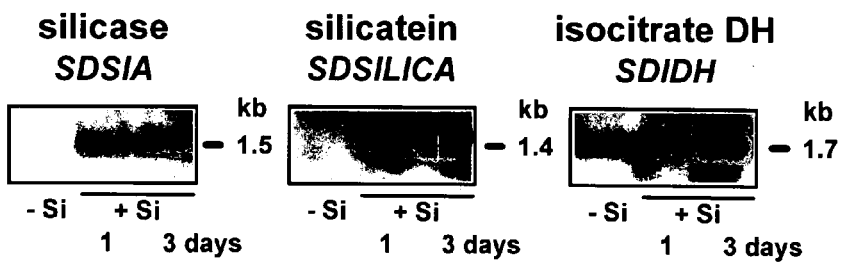
FIG. 7

[1] Reaction of silicase [hydration of $CO_2$]

$$CO_2 + H_2O \underset{}{\overset{\text{silicase}}{\rightleftharpoons}} H^+ + HCO_3^-$$

Effect on pH milieu
high metabolic activity
↓
oxidative respiration: $CO_2$ → release into the extracellular space
↓

$$CO_2 + H_2O \underset{}{\overset{\text{silicase}}{\rightleftharpoons}} H^+ + HCO_3^-$$

↓  ↓ modulation of pH

FIG. 8A

[2] Reaction of silicase [ester splitting]

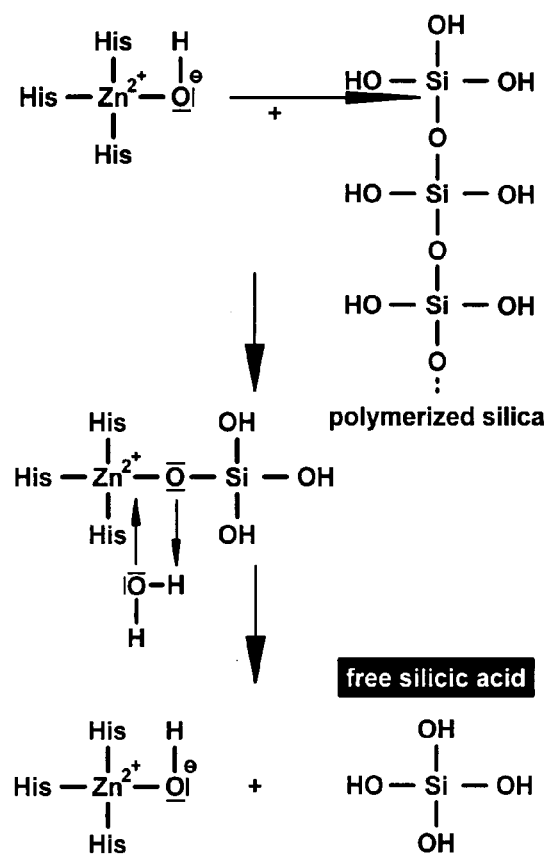

FIG. 8B

SEQUENCE LISTING

<160> NUMBER OF SEQ ID NOS: 2

<210> SEQ ID NO 1
<211> LENGTH: 1396
<212> TYPE: DNA
<213> ORGANISM: Suberites domuncula

<400> SEQUENCE: 1

```
gaattcggca cgagggacaa ctttgcataa cttttactgt ccatgtttaa cgtttagatc      60
tagtactagt agtctacaag aacaactgtc aacaactgtc agattatgtg tataaaccaa     120
gatgtctgca attcttaaga gaaacgtacc tatccaaaga gtcggtctcc cactgacctc     180
ctatgtcagt agatgggctt ctgctctgcc caccaggacc catcctttt acaagttggt      240 tgatgacagt accaccccag tgacaaggtc tactcttctc agtgctcata tggttgacac     300
cttgctagat gagaaccagc agagcagaca tgaaaaccaa cacacagaca cgtcttacaa     360
aatgtaccag ggattaaaat ttgttgtaaa gacgctgttt actccatcga aatgccaccg     420
tcacttctcc acatcagctc atttgtctgc catgggtcga catcaatccc ccatcaatat     480
aatcacctcc agtacgacca aaggaccgtc attgaaaccg ttaaaattta gcaagagttg     540
ggacaagcca gtaatcggca ccgtcaaaga tactggctat tatcttaaat ttgcaccaga     600
atctgcagca gagaagtgca cattgcatac gtacaatggt gaatatatcc tagatcattt     660
ccattatcac tgggggaaga aggatgggga aggagcagag catttcatcg atggaaaaca     720
atacgacatc gagttccact ttgtacataa aaaggttggg ttgactgatc cagatgctag     780
agacgctttt gctgttttgg gcgttttttgg aaaggccgac cctcgtttga agatcaatgg     840
aatctgggag ctactctcac cgtcaactgt cctgactgtc gactcaacac gaaacgtcgc     900
tgatgttgtt ccctctaagc ttctcccaag tgccagagac tatttttcact atgaaggttc     960 tttgaccaca cctacgtatg gtgaggttgt gcactggttt gttctcaatg aacccatagc    1020
tgtccctagt gagtatctgt cagctctgag acagatgcaa gctgacaaag aaggtactgt    1080
```

```
gattgactca aactatcgag agcttcaaga agtccacaat cgacctgtgc aacgatttaa    1140
gagtgatgag caagggagag gagaatttga cgatatttct aagaatgagg acattgtgga    1200
ggacttgtct aaattgtctg gtaactttat tagagagctg gtcaggaaga tatattggtg    1260
acctttttct acacttgtta gagttttagg ccagaataca tttcatcatt tggactgtta    1320
ttttgtgtac actgcttagc agtttatata aacactacaa tgccattatt ataatatagc    1380
caatgctgtg atttga                                                    1396
```

<210> SEQ ID NO 2
<211> LENGTH: 379
<212> TYPE: PRT
<213> ORGANISM: Suberites domuncula

<400> SEQUENCE: 2

```
Met Ser Ala Ile Leu Lys Arg Asn Val Pro Ile Gln Arg Val Gly Leu
1               5                   10                  15

Pro Leu Thr Ser Tyr Val Ser Arg Trp Ala Ser Ala Leu Pro Thr Arg
            20                  25                  30

Thr His Pro Phe Tyr Lys Leu Val Asp Asp Ser Thr Thr Pro Val Thr
        35                  40                  45

Arg Ser Thr Leu Leu Ser Ala His Met Val Asp Thr Leu Leu Asp Glu
    50                  55                  60

Asn Gln Gln Ser Arg His Glu Asn Gln His Thr Asp Thr Ser Tyr Lys
65                  70                  75                  80

Met Tyr Gln Gly Leu Lys Phe Val Val Lys Thr Leu Phe Thr Pro Ser
                85                  90                  95

Lys Cys His Arg His Phe Ser Ser Ala His Leu Ser Ala Met Gly
            100                 105                 110

Arg His Gln Ser Pro Ile Asn Ile Ile Thr Ser Ser Thr Thr Lys Gly
        115                 120                 125

Pro Ser Leu Lys Pro Leu Lys Phe Ser Lys Ser Trp Asp Lys Pro Val
    130                 135                 140

Ile Gly Thr Val Lys Asp Thr Gly Tyr Tyr Leu Lys Phe Ala Pro Glu
145                 150                 155                 160

Ser Ala Ala Glu Lys Cys Thr Leu His Thr Tyr Asn Gly Glu Tyr Ile
                165                 170                 175

Leu Asp His Phe His Tyr His Trp Gly Lys Lys Asp Gly Glu Gly Ala
            180                 185                 190

Glu His Phe Ile Asp Gly Lys Gln Tyr Asp Ile Glu Phe His Phe Val
        195                 200                 205

His Lys Lys Val Gly Leu Thr Asp Pro Asp Ala Arg Asp Ala Phe Ala
    210                 215                 220

Val Leu Gly Val Phe Gly Lys Ala Asp Pro Arg Leu Lys Ile Asn Gly
225                 230                 235                 240

Ile Trp Glu Leu Leu Ser Pro Ser Thr Val Leu Thr Val Asp Ser Thr
                245                 250                 255

Arg Asn Val Ala Asp Val Val Pro Ser Lys Leu Leu Pro Ser Ala Arg
            260                 265                 270

Asp Tyr Phe His Tyr Glu Gly Ser Leu Thr Thr Pro Thr Tyr Gly Glu
        275                 280                 285

Val Val His Trp Phe Val Leu Asn Glu Pro Ile Ala Val Pro Ser Glu
    290                 295                 300

Tyr Leu Ser Ala Leu Arg Gln Met Gln Ala Asp Lys Glu Gly Thr Val
```

-continued

```
305                 310                 315                 320
Ile Asp Ser Asn Tyr Arg Glu Leu Gln Glu Val His Asn Arg Pro Val
                325                 330                 335

Gln Arg Phe Lys Ser Asp Glu Gln Gly Arg Gly Glu Phe Asp Asp Ile
            340                 345                 350

Ser Lys Asn Glu Asp Ile Val Glu Asp Leu Ser Lys Leu Ser Gly Asn
        355                 360                 365

Phe Ile Arg Glu Leu Val Arg Lys Ile Tyr Trp
    370                 375
```

DECOMPOSITION AND MODIFICATION OF SILICATE AND SILICONE BY SILASE AND USE OF THE REVERSIBLE ENZYME

This application is a National Stage Application of International Application Number PCT/EP2003/010983, filed Oct. 2, 2003; which claims which claims priority to German Application No. 102 46 186.4, filed Oct. 3, 2002.

1. State of the Art

Silicon is the second-most element of the earth's crust and is present in all kinds of different compounds. Silicon compounds do not only represent most of the species of this class of minerals, but are also very important from an economical point of view. Technically used materials that are composed of silicates are, for example, glass, porcelain, enamel, clay products, cement and water glass. Some silicates exhibit catalytic properties. Their diversity in structures and the technical uses are further expanded, if other elements, in particular aluminum, occupy some of the lattice positions that are otherwise occupied by silicon. Thus, the alumo silicates, belonging to which are feldspars and zeolithes, have importance due to, amongst others, their molecular sieve and ions exchange properties. Other silicon-compounds such as the silicones (siloxanes), amongst others, also are of medical importance, such as for the production of implants.

1.1. Silicon Dioxide

Silicon dioxide ($SiO_2$) can be found both in crystallized and amorphous form. Quartz, tridymite, and cristobalite, amongst others, belong to the different forms of crystalline $SiO_2$. Achat, opal, and flint stone represent amorphous silicon dioxide-materials. In all these silicon has the coordination-number 4 and is tetraedrically surrounded by four oxygen-atoms.

Furthermore, the shells of diatoms (diatomeae) and the needles (spicules) of diatomeous sponges consist out of amorphous $SiO_2$.

1.2. Silicic Acids and Silicates

The tetraedrically-built $[SiO_2]^{4-}$-ion tends to polymerization by linking $SiO_4$-Units, wherein in each case two Si-atoms are linked together by an O-atom. In this, at first ortho-disilicic acid (pyro-silicic acid; $H_6Si_2O_7$) is formed from ortho-silicic acid by condensation (splitting off water). The further condensation via the poly-silicic acids leads to the meta-silicic acids $[(H_2SiO_3)]_n$. In case of smaller numbers of $SiO_4$-units (n=3, 4 or 6) also ring-shaped molecules can be formed through this.

The salts of the silicic acids, the alkali silicates, which, for example, can be obtained by melting of quartz with soda, brine or potassium carbonate, in addition to $[SiO_4]^{4-}$ anions, also contain $[Si_2O_7]^{6-}$ and $[Si_3O_{10}]^{8-}$ anions, and larger anions. Such ortho-disilicic acids (ortho-silicates), having the structure $Me_2SiO_4$, contain single $[SiO_4]^{4-}$ anions. After acidification of such an alkali silicate-solution, the acid molecules that are formed by the uptake of protons, condensate with each other to form poly-silicic acids, whereby the solution becomes gel-like. Upon further progress of the condensation, three-dimensional structures are formed from the chains or nets that are first obtained, that correspond to the composition $SiO_2$.

The silicates can be classified into: 1.) Silicates with discrete anions, namely 1 a) island-silicates (ortho-silicates having the anion $[SiO_4]^{2-}$; example: phenacite, olivine, zirconium), 1 b) Group-silicates (Linkage of the $SiO_4$-tetraeders to form short chain units: example: di-silicates and tri-silicates) and 1 c) Ring-silicates (the $SiO_4$-tetraeders are arranged in ring form, example: benitoid with 3-ring, axinite with 4-ring, and beryllium with 6-ring), 2. Chain-silicates and ribbon-silicates (chain-like $SiO_4$-tetraeders are bound to each other; representing polymers of the anions $[SiO_3]^{2-}$, and ribbon-like molecules that are formed by linking several $SiO_4$-chains; examples: homblende, asbestos). 3. Layer or sheet-silicate (made from even layers of tetraeders that represent polymers of the anions $[Si_4O_{10}]^{4-}$ and are held together by cations stored in-between; examples: talcum, caolinit, and 4. Scaffold-silicates (linkage of the tetraedic $SiO_4$-groups into three-dimensional lattices; example: different modifications of silicon dioxide, such as feldspatuses).

General literature: Hinz, Silicat-Lexikon (2 Bd.), Berlin: Akademie Verl. 1985; Liebau, Structural Chemistry of Silicates, Berlin: Springer 1985; Petzold and Hinz, Einführung in die Grundlagen der Silicatchemie, Stuttgart: Enke 1979; CD Rompp Chemie Lexikon-Version 1.0, Stuttgart/New York: Georg Thieme Verlag 1995.

1.3. Silicones

Different silicones (siloxanes) are generated by a partial replacement of the OH-group in the silicic acid by single-bond organylic residues that do not participate in the condensation process. They are classified into: 1.) linear polysiloxanes (construction type: $R_3SiO[R_2SiO]_nSiR_3$), 2) branched polysiloxanes (with tri-functional or tetra-functional siloxane-units at their branching sites), 3) cyclic polysiloxanes (from di-functional siloxane-units) and 4) cross linked polymers (chain- or ring-form molecules are linked into two- or three-dimensional networks).

Silicones are important technical materials. The viscosity of the high molecular weight silicones (silicone oils) consisting of chain-macromolecules, increases with increasing chain length. Silicones that are cross-linked to a low extent exhibit rubber-elasticity (silicone rubber), highly cross-linked chains are resin-like (silicone resins).

1.4. Silicatein

Some of the above-mentioned silicon compounds can only be produced in a cost-intensive manner or are present only in small amounts as mineral resources, respectively, and can therefore only be isolated with considerable effort. The process of the chemical synthesis of silicates requires drastic conditions, such as high pressure and high temperature.

In contrast, with the aid of specific enzymes organisms (in particular sponges and algae) are able to form silicate scaffolds under natural conditions, i.e. at low temperature and low pressure. The advantages of this pathway are: high specificity, coordinated formation, adjustability, and the possibility for synthesizing nanostructures.

The isolation and purification of a silicate-forming enzyme (silicatein) was recently described for the first time: Shimizu, K., et al., Proc. Natl. Acad. Sci. USA 95: 6234-6238 (1998).

Nevertheless, this results in the problem that the isolation and the purification of the enzyme (silicatein) is time-consuming and laborious, and that only relatively low amounts can be achieved.

One possible approach is the synthesis of the recombinant protein (recombinant silicatein) with the aid of the known cDNA- or gene-sequence. This allows for the effective enzymatic synthesis of silicates.

In case of the production of the recombinant silicateins from the sponges *Suberites domuncula* and *Tethya aurantia,* the problem occurred that by using the methods according to the state of the art only very low yields could be achieved and that the recombinant protein exhibited only low enzymatic activity. The present invention describes that, by specific modification of the expression conditions, recombinant silicatein can be produced in high yields and with high specific activity. Furthermore, the modified recombinant enzyme exhibits a higher pH and temperature stability than the natural one and the recombinant one having a complete cDNA-sequence. The modified recombinant protein furthermore exhibits an enzymatic activity over a broad pH (4.5-10), in contrast to the natural and recombinant protein with complete cDNA-sequence that is active at pH-values in the neutral range (pH 7.0).

By way of production of a specific polyclonal antibody and subsequent coupling to a solid phase, a fast and effective affinity-chromatography purification of the enzyme can be achieved.

The use of fusion proteins and the application of different starting substrates lead to numerous possibilities for variations and technical applications.

1.4. Biomineralisation (Formation of Biogenic Silicon Dioxide) in Siliceous Sponges Many silicon compounds can only be produced in a cost-intensive manner, The process of the chemical synthesis of the silicates often requires drastic conditions, such as high pressure and high temperature. In contrast, siliceous sponges—in addition to diatoms—are able to form silicate scaffolds under mild conditions with the aid of specific enzymes, i.e. at relatively low temperature and low pressure. Furthermore, in these organisms the SiO2-synthesis is characterized by a high specificity, controllability and the possibility of the synthesis of defined microstructures (nanostructures)

The main elements of the skeleton of the siliceous sponges are the needle-like spicules that in the group of the demospongiae (horn sponges) and hexactinellidae (glass sponges) consist out of amorphous non-crystalline silicon dioxide. The demospongiae and hexactinellidae are the only metazoes that have silicon dioxide instead of calcium in their skeleton.

The opaque silicon dioxide in the spicules of the siliceous sponges contains 6-13% water resulting in the approximate formula $(SiO_2)_2 5H_2O$ (Schwab D W, Shore R E (1971) Mechanism of internal stratification of siliceous spicules. Nature 232: 501-502).

An enzyme that is involved in the synthesis of the $SiO_2$-skeletton in silicate forming organisms, and its technical use was described (PCT/US99/30601. Methods, compositions, and biomimetic catalysts, such as silicateins and block copolypeptides, used to catalyze and spatially direct the polycondensation of silicon alkoxide, metal alkoxide, and their organic conjugates to make silica, polysiloxanes, polymetallo-oxanes, and mixed poly (silicon/metallo) oxane materials under environmentally benign conditions. Inventors/applicants: Morse D E, Stucky G D, Deming, T D, Cha J, Shimizu K, Zhou Y; D E 10037270 A 1. Silicatein-vermittelte Synthesis von amorphen Silicaten und Siloxane and ihre Verwendung. Deutsches Patentamt 2000. Applicant and inventor: Müller W E G, Lorenz B, Krasko A, Schröder H C; PCT/EP01/08423. Silicatein-mediated synthesis of amorphous silicates and siloxane and use thereof. Inventors/Applicants: Müller W E G, Lorenz B, Krasko A, Schröder H C). This enzyme was cloned from the marine siliceous sponge *Suberites domuncula* (Krasko A, Batel R, Schröder H C, Müller I M, Müller W E G (2000) Expression of silicatein and collagen genes in the marine sponge *S. domuncula* is controlled by silicate and myotrophin. Europ J Biochem 267 : 4878-4887). The enzyme being isolated from natural sources ("silicatein") is able to synthesize amorphous silicon dioxide (poly(silicic acids) and poly(silicates)) from organic silicon compounds (alkoxy silanes) (Cha J N, Shimizu K, Zhou Y, Christianssen S C, Chmelka B F, Stucky G D, Morse D E (1999) Silicatein filaments and subunits from a marine sponge direct the polymerization of silica and silicones in vitro. Proc Natl Acad Sci USA 96: 361-365).

Surprisingly, the inventors—first in the marine sponge *S. domuncula* as a model system—could discover an enzyme (designated: "silicase") being able to decompose both amorphous as well as crystalline silicon dioxide.

This enzyme that is involved in the catabolism of silicon dioxide in sponges was identified using the technique of "differential display" of the mRNA by using the in vitro Primmorph-cell culture system (see below).

The silicase can perform two functions: first it has the ability (i)—in analogy to the carbonic anhydrase—to dissolve lime-material, and (ii)—and this was surprising—also to dissolve silicon dioxide by forming silicic acid. Thus, the silicase—as found first in *S. domuncula*—is able to engage both in the catabolism of lime-containing material as well as in the catabolism of the silicic acid-containing spicules.

The present invention is furthermore novel in that the silicase-gene can be induced by an increase of the silicon-concentrations in the medium (to commonly 60 μM) (see FIG. 7).

According to a further aspect of the present invention, generally a method for the in vitro or in vivo degradation of amorphous or crystalline silicone dioxide (condensation products of the silicic acid, silicates), silicones and other silicon (IV)- or metal (IV)-compounds as well as of mixed polymers of these compounds is provided, wherein a polypeptide or a metal complex of a polypeptide is used for the degradation, characterized in that the polypeptide comprises an animal, bacterial, plant or fungal carbonic anhydrase domain that exhibits a sequence similarity of at least 25% (see FIGS. 3A and 3B) to the sequence shown in SEQ ID No. 1. Until now, it was not known that such carbonic anhydrase-domains-containing enzymes are able to decompose such silicates or silicones. Due to the reversibility of the process a further aspect of the present invention relates to a method for the synthesis of amorphous silicone dioxide (condensation products of the silicic acid, silicates), silicones and other silicon (IV)- or metal (IV)-compounds as well as of mixed polymers of these compounds, wherein a polypeptide or a metal complex of a polypeptide is used for the synthesis, characterized in that the polypeptide comprises an animal, bacterial, plant or fungal carbonic anhydrase domain that exhibits a sequence similarity of at least 25% to the sequence shown in SEQ ID No. 1.

Preferred is a method according to the present invention that is characterized in that compounds such as silicic acids, monoalkoxy silantrioles, dialkoxy silandioles, trialkoxy silanoles, tetraalkoxy silanes, alkyl- or aryl-silantrioles, alkyl- or aryl-monoalkoxy silandioles, alkyl- or aryl-dialkoxy silanoles, alkyl- or aryl-trialkoxy silanes or other metal(IV)-compounds are used as reactants (substrates) for the synthesis. By using defined mixtures of the compounds mixed polymers having a defined composition can be produced.

According to a further aspect of the present invention a formation of defined two- and three-dimensional structures can occur by the polypeptide or a metal complex of the polypeptide or the binding of the polypeptide or a metal complexes of the polypeptide to other molecules or the surfaces of glass, metals, metal oxides, plastics, biopolymers or other materials as a template.

According to a further aspect of the present invention a method for the modification of a silicic acid or silicon(IV)- or metal (IV)-compound containing structure or surface is provided, wherein a polypeptide or a metal complex of a polypeptide is used for the modification, characterized in that the polypeptide comprises an animal, bacterial, plant or fungal carbonic anhydrase domain that exhibits a sequence similarity of at least 25% to the sequence shown in SEQ ID No. 1. Preferably, the silicic acid-containing structure or surface is present in form of a precious stone or semi-precious stone.

Preferred is a method according to the present invention, wherein the modification comprises a smoothing, an etching or the production of burrows of the silicic acid or silicon (IV)- or metal(IV)-compound-containing structure or surface by the polypeptide or a metal complex of the polypeptide.

A further aspect of the present invention relates to a chemical compound or silicic acid-containing structure or surface, obtained according to a method of the present invention, in particular in the form of a precious stone or semi-precious stone.

A further aspect of the present invention also relates to a polypeptide of a silicase from *Suberites domuncula* according to SEQ ID Nr. 1 or a polypeptide being homologous thereto, which in the amino acid sequence of the carbonic anhydrase domain exhibits a sequence similarity of at least 25% to the sequence shown in SEQ ID No. 1, a metal complex of the polypeptide, or parts thereof.

A further aspect of the present invention also relates to a nucleic acid, in particular according to SEQ ID No. 2, characterized in that it essentially encodes for a polypeptide according to the invention. The nucleic acid according to the invention can be characterized in that it is present in the form of a DNA, cDNA, RNA or mixtures thereof and can be characterized in that the sequence of the nucleic acid has at least one intron and/or a polyA-sequence. Another aspect of the present invention relates to the nucleic acid according to the invention in the form of its complementary "antisense"-sequence.

A still further aspect of the present invention also relates to a nucleic acid according to the invention in the form of a (a) fusion protein-(chimeric protein) construct, (b) construct having a separate protein-expression (protease-cleavage site) or (c) construct having a separate protein-expression (cassette-expression). The nucleic acid according to the invention can be synthetically produced. Respective methods are well known in the state of the art.

A further aspect of the present invention relates to a vector, preferably in the form of a plasmid, shuttle vector, phagemid, cosmid, expression vector, retroviral vector, adenoviral vector or particle, nanoparticle or liposome, comprising a nucleic acid according to the present invention. Furthermore, vectors for the transfer of proteins can be provided, preferably in the form of a nanoparticle or liposome, comprising a polypeptide according to the present invention.

According to a further aspect of the present invention a host cell, transfected with a vector or infected or transduced with a particle according to the invention, is provided. Said host cell can be characterized in that it expresses a polypeptide according to claim 1, a metal complex of the polypeptide or parts thereof. All know host cell-organisms are suitable as host cells, such as, amongst others, yeasts, fungi, sponges, bacteria, CHO-cells or insect cells.

The polypeptide according to the invention can be characterized in that the polypeptide has been synthetically produced or that the polypeptide or the metal complex of the polypeptide is present in a prokaryotic or eukaryotic cell extract or lysate. The cell extract or lysate can be obtained from a cell ex vivo or ex vitro, for example a recombinant bacterial cell or a marine sponge.

The polypeptide according to the invention can be purified according to common methods known in the state of the art, and therefore can be present essentially free of other proteins.

A further aspect of the present invention then relates to a method for identifying of inhibitors or activators of a polypeptide of a silicase from *Suberites domuncula* according to SEQ ID No. 1 or a polypeptide being homologous thereto that in the amino acid sequence of the carbonic anhydrase domain has at least 25% sequence similarity to the sequence shown in SEQ ID No. 1, wherein a) a polypeptide of a silicase from *Suberites domuncula* according to SEQ ID No. 1 or a polypeptide being homologous thereto that in the amino acid sequence of the carbonic anhydrase domain has at least 25% sequence similarity to the sequence shown in SEQ ID No. 1 is provided, b) the polypeptide from step a) is contacted wit a potential inhibitor or activator, and c) the ability of the polypeptide is measured to degrade or synthesize silicate or silicones. With this method valuable substances can be identified that are possibly suited as therapeutics (for this, see below). Methods for the identification of such substances are known to the person of skill, and include, for example, the use of radioactively labeled or enzymatically labeled candidate-compounds. Methods for measuring the activity of the silicase are described in the following and can readily be modified by the person of skill in view of a testing format. Thereby, an inhibitor lowers the activity of the enzyme essentially completely, an activator induces an activity or amplifies it above the baseline.

According to an alternative of the method the polypeptide of a silicase from *Suberites domuncula* according to SEQ ID No. 1 or a polypeptide being homologous thereto that in the amino acid sequence of the carbonic anhydrase domain has at least 25% sequence similarity to the sequence shown in SEQ ID No. 1 can be provided in vivo, in a cellular extract or lysate or in purified form.

A still further aspect of the present invention relates to a method for producing a pharmaceutical composition, comprising a) identifying of an inhibitor or activator according to claim 25 or 26 and b) mixing of the identified inhibitor or activator with a pharmaceutically acceptable carrier or excipient. By means of this composition, valuable pharmaceutics are provided that, such as for example the polypeptide or a nucleic acid or pharmaceutical composition can be used for the prevention or therapy of silicosis. Preferred is a use, wherein the prevention and therapy of silicosis occurs by dissolving of quartz crystals. Furthermore, the use of polypeptide or a nucleic acid or pharmaceutical composition according to the invention for the resorption or for modulating the resorbability of silicones and silicone implants can take place. Finally, the present invention can be used for transfecting cells with nucleic acids according to the invention for the resorption or for modulating the resorbability of silicones and silicone implants. The above indicated uses and the methods therefore are known to person of skill and can readily be adjusted to the needs and requirements as present here.

1.5. Cloning of the Gene Encoding the Silicase

By use of the technique of the "Differential Display" a cDNA was identified encoding for a carbonic anhydrase. For carbonic anhydrases until now only an involvement in the regulation of the pH, the $HCO_3^-$-reabsorption and the $CO_2$-expiration was known, but not an involvement in the—yet unknown—enzymatic dissolution of silicon dioxide-materials.

The cDNA encoding for the silicase from the marine sponge *S. domuncula* (designated: SDSIA) as well as the polypeptide derived from the nucleotide sequence (designated: SIA_SUBDO) have the following properties. Length of the cDNA: 1395 nucleotides (nt); open reading frame: from $nt_{122}$-$nt_{124}$ to $nt_{1259}$-$nt_{1261}$ (Stop codon); length of the polypeptide: 379 amino acids; relative molecular mass ($M_r$) of the polypeptide: 43131; isoelectric point (pI): 6.5 (calculated with: PC/GENE (1995) Data Banks CD-ROM; Release 14.0. IntelliGenetics, Inc. Mountain View, Calif.).

The Northern-blot-analysis with the sponge SDSIA-clone as a probe results in a band of 1.5 kb.

FIG. 2B shows the nucleotide sequence of the sponge-silicase-cDNA—identified with the aid of the differential display technique—, and FIGS. 2A and 2B, as well as FIG. 3A show the polypeptide derived from the nucleotide sequence of the sponge-silicase (SIA_SUBDO).

The derived amino acid sequence of the sponge-silicase has a large similarity to the amino acid sequences of the carbonic anhydrase-family. Until now, no more than seven isoenzymes of carbonic anhydrases were identified in humans (Sun M K, Alkon D L (2002) Carbonic anhydrase gating of attention: memory therapy and enhancement. Trends Pharmac Sci 23: 83-89). The "Expect value" [E] (Coligan J E, Dunn B M, Ploegh H L, Speicher D W, Wingfield P T (2000) Current protocols in protein science. John Wiley & Sons, Chichester) of the sponge-silicase with the human carbonic anhydrase II (CAH2_HUMAN; P00918) is $2e^{-29}$. The eukaryotic-type-carbonic anhydrase domain (PFAM00194 [www.ncbi.nlm.nig.gov]) in the sponge-silicase is found in the amino acid-region of aa87 to aa335 (FIG. 3A). The alignment of the sponge-silicase with the human carbonic anhydrase II shows that most of the characteristic amino acids that form the eukaryotic-type-carbonic anhydrase-signature (Fujikawa-Adachi K, Nishimoril, Taguchi T, Yuri K, Onishi S (1999) cDNA sequence, mRNA expression, and chromosomal localization of human carbonic anhydrase-related protein, CA-RPXI. Biochim Biophys Acta 1431: 518-524 ; Okamoto N, Fujikawa-Adachi K, Nishimori I, Taniuchi K, Onishi S (2001) cDNA sequence of human carbonic anhydrase-related protein CA-RP X and XI in human brain. Biochim Biophys Acta 1518: 311-316) are also present in the sponge-silicase. Nevertheless, in the sponge-sequence the amino acid residues 192 (alanine), 205 (phenylalanine) and 207 (phenylalanine) are replaced (FIG. 3A).

The carbonic anhydrases constitute a family of zinc metal-enzymes that are involved in the reversible hydration of $CO_2$ (Sly W S, Hu P Y (1995) Human carbonic anhydrases and carbonic anhydrase deficiencies. Annu. Rev. Biochem. 64: 375-401). The three conserved histidine residues are found in the silicase at the amino acids aa181, aa183, and aa206 (FIG. 3A).

1.6. Phylogenetic Analysis of the Silicase

Figure 3B:
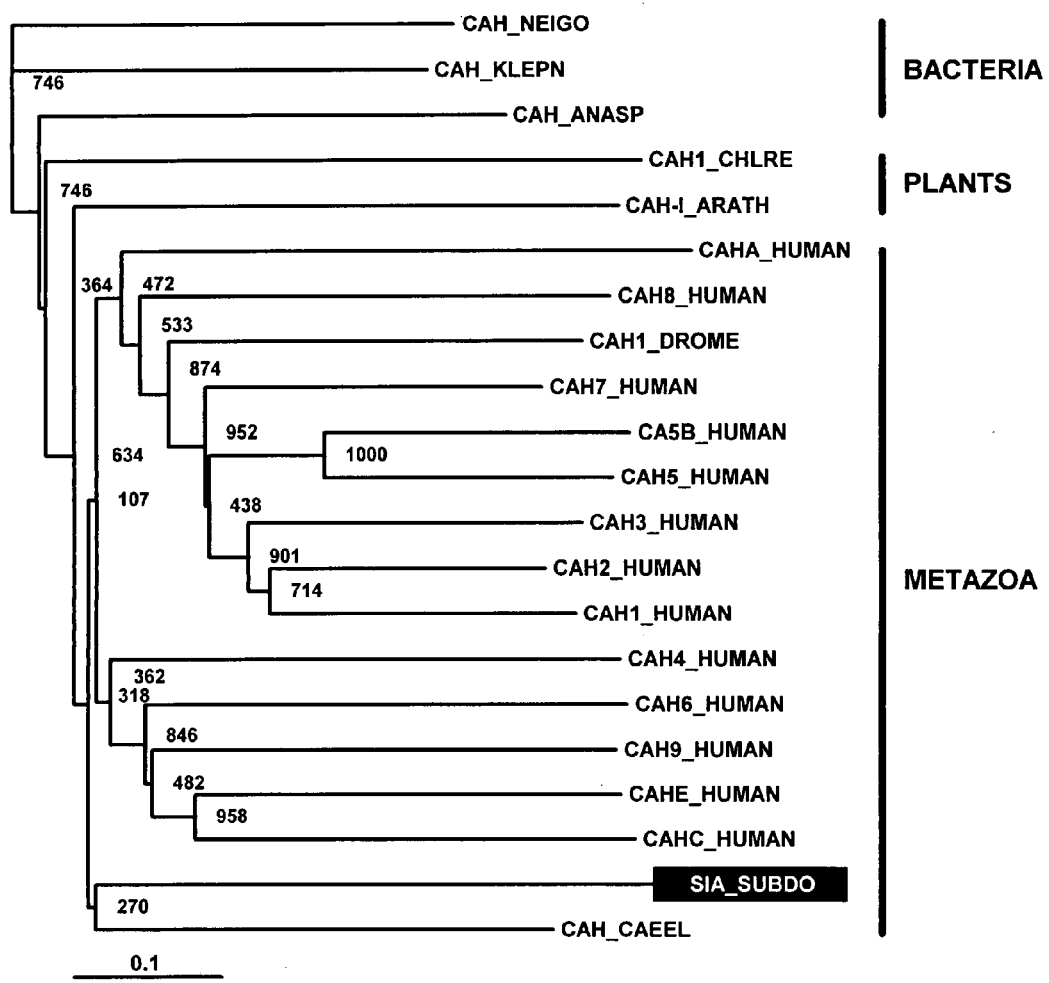

FIG. 3B shows the position of the sponge-silicase amongst different elected representatives of the carbonic anhydrase-family (phylogenetic tree; "rooted tree" with the bacterial carbonic anhydrase-sequences of *Neisseria gonorrhoeae*). The sponge-silicase together with the carbonic anhydrase of *Caenorhabditis elegans* form the base for the carbonic anhydrases of the other metazoes. The metazoic enzymes are separated from the plant-enzymes and also from the bacterial enzymes.

2. Production of Silicase

Die silicase can be purified from tissues or cells or can be recombinantly produced.

2.1. Purification of the Silicase From Natural Sources

All steps are performed at 4° C. For the purification of the silicase (or carbonic anhydrase or carbonic anhydrase-related enzyme) the homogenized tissue is—for example in a Tris-$SO_4$/Sodiumsulfate-buffer (pH 8.7)—(or are cells that are homogenized in this buffer) centrifuged and an affinity chromatography-matrix such as for example CM-Bio-Gel A, coupled with p-aminomethyl benzene sulfonic acid amide is added to the supernatant as obtained. Then, the suspension is incubated on a rotating shaker (for example for 24 h). The affinity gel is then collected by suction via a glass filter, and washed with a buffer (for example 0.1 M Tris-$SO_4$, pH 8.7 containing 0.2 M $Na_2SO_4$, 1 mM benzamidine and 20% glycerol). Subsequently it is suitable to add a second wash step with the same buffer at a lower pH (for example pH 7.0) in order to remove unspecifically bound proteins. The gel is then transferred into a column and washed with the same buffer (pH 7.0). For an elution of the enzyme for example a 0.1 M Tris-$SO_4$-buffer, pH 7,0, containing 0.4 M $NaN_3$, 1 mM benzamidine and 20% glycerol can be used. The eluted enzyme protein is then dialysed against for example a 10 mM Tris-$SO_4$-buffer, pH 7.5, containing 1 mM benzamidine, and thereafter added on an ion exchange column (for example DEAE-Sephacel) which, for example, has been equilibrated with 10 mM Tris-$SO_4$-buffer, pH 7.5. After the washing with the same buffer the enzyme is eluted by applying a linear salt-gradient (for example 0 to 0.1 M $Na_2SO_4$) and collected. With the aid of this procedure the silicase, amongst others, can be purifies from the sponge *S. domuncula*.

2.2. Production of the Recombinant Silicase 2.2.1. Cloning of the cDNAs from Marine Sponges Performing the technique of the "Differential Display" of the mRNA/transcripts is state of the art (Müller W E G, Krasko A, Skorokhod A, Bünz C, Grebenjuk V A, Steffen R, Batel R, Müller I M, Schröder H C (2002) Histocompatibility reaction in the sponge Suberites domuncula on tissue and cellular level: central role of the allograft inflammatory factor 1. Immunogenetics 54,48-58). Total-RNA is isolated from control cultures (held at a low silicon-concentration of 5pM) as well as from cultures treated in the presence of 60 μM silicon by using the TRIzol reagent (GibcoBRL). The synthesis of the first cDNA-strand is performed with "anchored" oligo (dT)-primers and AMV reverse transcriptase according to the protocol of the manufacturer (Promega). After the synthesis of the first strand the resulting cDNA is diluted tenfold with $H_2O$, and an aliquot part thereof (2 μl) is subjected to the polymerase-chain-reaction (PCR). The reaction is performed in a volume of 20 pl after the addition of the "arbitrary" primers 1 (5'-GTGATCGCAG-3') or 2 (5'-CTTGATTGCC-3') as well as of 2 μM dNTP, $T_{11}GC$, 5 units BioThem Polymerase (Genecraft), and [α-32P] dATP performed. The following reaction conditions have could be found as suitable for the PCR: initial denaturation at 95° C. for 5 minutes, then 40 amplification cycles each at 95° C. for 20 seconds, 42° C. for 120 seconds, 72° C. for 30 seconds, followed by a final incubation of 10 minutes at 72° C. The samples are then separated in a 5% polyacrylamide gel (in 1×TBE). After the run the gel is dried and exposed for 4 days to an x-ray film. The interesting bands that are identified in the autoradiogram are cut out, boiled for 15 minutes in 200 ul $H_2O$, chilled on ice and centrifuged for 10 minutes at 14000×g. The resulting supernatants are supplemented with the same volume of 10 M ammonium acetate, 20 μg/ml tRNA and precipitated with 2.5 volumes of ethanol at −80° C. over night. The cDNA-pellets are washed three times in 75% ethanol, and dissolved in 20 μl $H_2O$.

Approximately 2 μl of the eluted bands are re-amplified in 50 μl-reaction-preparations by using the above described primers under the same conditions, are subcloned in a pGEM-T-vector (Promega), and sequenced.

Those transcripts are selected that are differentially expressed, i.e. that are additionally contained in the gels with the RNAs of cells that have been treated with 60 μM silica (FIG. 1). The identified cDNAs/transcripts are compared with sequences contained in the BLAST data base. In the example given in FIG. 1 the following molecules showed the largest relation: Calcium/Calmodulin-dependent protein kinase (CaM Kinase)II gamma (XM_044349; Expect value [E]:$1e^{-16}$); hypothetic protein (XP_101359,E 1,6); MUC3B mucin (AJ291390, E 0,20); hypothetic protein (XP_067115, E 5,9); hypothetic protein (XP_090138, E 2,9); ATP-binding cassette, subfamily A member 4 (XM_001290, E 1,6); polypeptide similar to the zinc finger protein 91 (XM_091947, E 3,1); hypothetic protein (XP_104250, E 0,48), hypothetic protein (XP_169372, E 8,6); hypothetic protein (XP_104250, E 4,1), hypothetic protein (XP_098020, E 3,3) and hypothetic protein (XP_169372, E 8,6).

In addition to these sequences the silicase was identified as additional transcript and analyzed in more detail.

The silicase gene can also be identified from cDNA-libraries, e.g. in ZapExpress and in *Escherichia coli* XL1-Blue MRF', with suitable degenerated primers by means of the PCR-technique; for this, the corresponding vector-specific primers are used. The synthesis products as obtained are used for screening in the den respective cDNA-libraries. Then, the identified clones are subcloned in a vector (for example pGem-7) and subsequently sequenced.

2.2.2. Expression and Isolation of the Recombinant Silicase

The production of the recombinant silicase (designated: rSIA_SUBDO) preferably occurs in *E. coli*. Nevertheless, also the production in yeasts and mammalian cells is possible and was successfully done. In the following as an example the expression of the SDSIA-gene of *S. domuncula* in *E. coli* using the "GST (glutathione-S-transferase) fusion"-system (Amersham) described. In the example two inserts are used in order to eliminate potential effects of signal peptides during the expression; one insert comprises the whole derived protein (long form; from amino acid $aa_1$ to the amino acid $aa_{379}$) and the other insert only the amino acids $aa_{96}$ to $aa_{379}$ (short Form) (FIG. 3A). The corresponding clones are designated as SDSIA-l and SDSIA-s. They are cloned in a corresponding vector, e.g. into the plasmid pGEX-4T-2, containing the glutathione-S-transferase (GST)-gene of *Schistosoma japonicum*. Also other expression vectors have proven suitable. After transformation von *E. coli* the expression of the silicase is usually induced by IPTG (isopropyl-β-D-thiogalactopyranoside), and performed in the presence of 1 mM $ZnSO_4$ for 4 or 6 hours at 37° C. (Ausubel F M, Brent R, Kingston R E, Moore D D, Smith J A, Seidmann J G, Struhl K (1995) Current Protocols in Molecular Biology. John Wiley and Sons, New York). The obtained GST-fusions proteins with the designation SIA_SUBDO-1 (long form; $M_r$ 69 kDa) or rSIA SUBDO-s (short form; $M_r$ 58 kDa) are, e.g. purified by affinity chromatography on glutathione-Sepharose 4B. For a separation of the glutathione-S-transferase from the recombinant sponge-silicase the fusions proteins are cleaved with thrombin (10 units/mg). The proteins are then subjected to gel electrophoresis in the presence of 2-mercaptoethanol. The gel electrophoresis can be performed in 10% polyacrylamide gels with 0.1% $NaDodSO_4$ (PAGE). The gels are stained with Coomassie Brillant blue.

Figure 4:
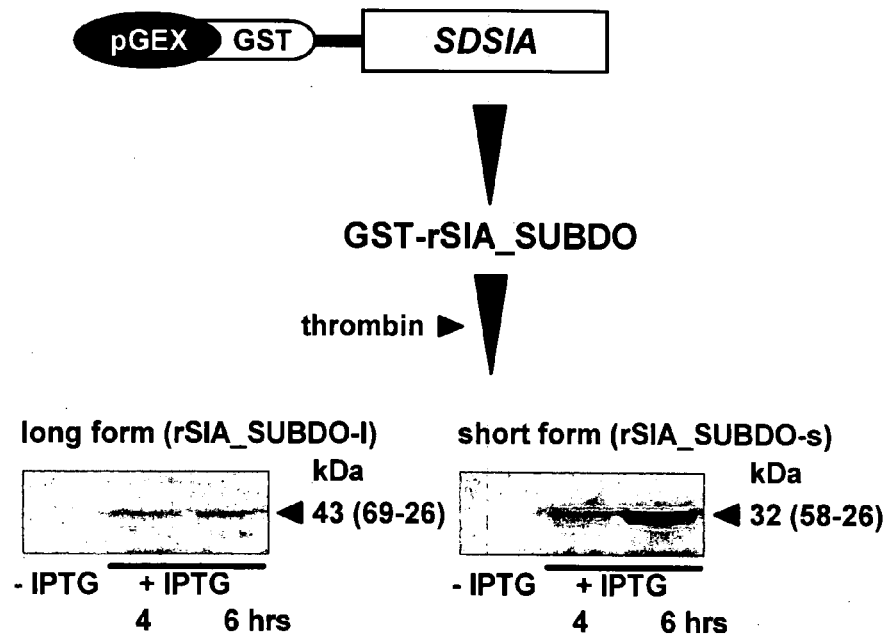

After the cleavage, purification, and subsequent PAGE the long form (rSIA_SUBDO-1 [43 kDa]) and the short form (rSIA_SUBDO-s [32 kDa]) of the recombinant proteins are obtained (FIG. 4).

2.2.3. Expression and Isolation of the Recombinant Silicase From Other Organisms In agreement with the above described strategy, the isolation, cloning, and expression of the silicase-cDNA from other organisms can also be performed, for example from (silicon dioxide-producing) diatoms (e.g. *Cylindrotheca fusiformis*). The method of obtaining diatoms in axenic cultures is state of the art (Kröger N, Bergsdorf C, Sumper M (1996) Europ J Biochem 239: 259-264).

2.3. Isolation and Purification of the Silicase by Means of Antibody

Following extraction or partial purification according to the above described methods the silicase is purified on an antibody-affinity matrix. The affinity matrix is produced in that a silicase-specific antibody is immobilized on a solid phase (CNBr-activated sepharose or other suitable carrier). As antibody, monoclonal or polyclonal antibodies against the silicase are used that are produced according to standard methods (Osterman L A (1984) Methods of Protein and Nucleic Acid Research, Vol 2, Springer-Verlag, Berlin). The coupling of the antibody to the matrix of the column is done in accordance with the instructions of the manufacturer (Pharmacia). The elution of the pure silicase occurs by a change of pH or ionic strength.

3. Determination of the Silicase-activity

In the following only the activities are given that have been found for the short form of the recombinant sponge-silicase (rSIA_SUBDO-s).

3.1. Carbonic Anhydrase-activity

For determining the carbonic anhydrase-activity of the rSIA_SUBDO-s, an assay can be used that is based on the hydrolysis of p-nitrophenylacetate (Armstrong J M, Myers D V, Verpoorte J A, Edsall J T (1966) Purification and properties of human erythrocyte carbonic anhydrase. J Biol Chem 241: 5137-5149). 0.5 ml of a 3 mM p-nitrophenylacetate-solution (Sigma) are mixed with 0.05 ml of a 0.3 mM Tris-HCl-buffer (pH 7.6). After pre-incubation at 25° C. for 5 minutes 50 μl of the recombinant silicase (rSIA_SUBDO) are added and the increase of the extinction at 348 nm is determined over a period of 5 minutes.

Figure 5:
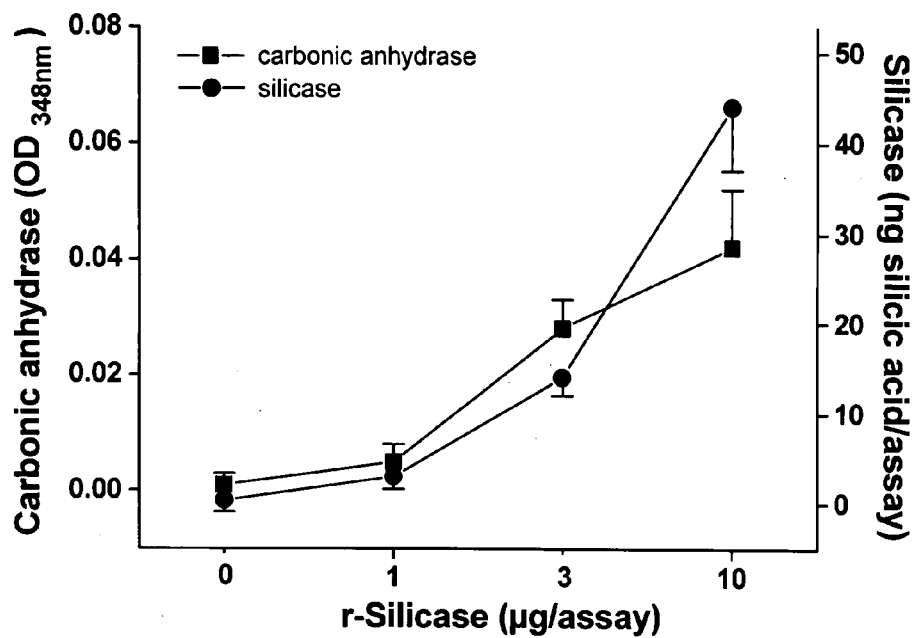

FIG. 5 shows that the activity of the recombinant silicase depends from the concentration of the enzyme in the assay. The activity of the enzyme is given optical density (OD)-units per minute. The addition of 1 μg silicase per assay (0.56 μl) resulted in an activity of 0.005 $OD_{348\ nm}$, that increased with increasing protein concentration up to 0.04 $OD_{348\ nm}$.

3.2. Silicase-activity

As substrate (amorphous silicon dioxide) for the silicase, for example, spicules of *S. domuncula* are suitable. The spicules can be obtained from sponge tissue by 12-hour incubation in the presence of ethylene diamine tetraacetic acid (20 mM, in PBS; PBS=phosphate buffer-salt-solution, consisting of 1.15 mM $KH_2PO_4$, 8.1 mM $Na_2HPO_4$, 137 mM NaCl and 2.7 mM KCl). After washing with distilled water and with ethanol (two times) the spicules are dried (56° C.) and then grinded to a powder in a mortar.

The silicase-activity can be determined as follows. Commonly, 100 μg of the dried spicules (powder) are added to a suitable buffer, such as 50 mM Tris-HCl-buffer (pH 7.2; 10 mM DL-dithiothreitol, 100 mM NaCl) and 0.5 mM $ZnSO_4$ in 2 ml Eppendorf-tubes. Then, usually 50 µl of the recombinant silicase are added, and incubated at 25° C. (the incubation is possible also at other temperatures between 5° C. and about 65° C.). The average incubation time is 60 minutes. For a quantitative determination of the amount of dissolved silicon dioxide, the non dissolved spicules are spun off (14000×g; 15 minutes; 4° C.). The released soluble silicic acid can be quantitatively determined e.g. with the aid of a molybdenum-supported determination methods such as e.g. the colorimetric "Silicon Test" (Merck; 1.14794). In this case, the amount of silicic acid is calculated from the values of extinction at 810 nm based on a calibration curve with a silicon standard (Merck 1.09947).

FIG. 5 shows that the recombinant silicase catalyses the degradation (dissolution) of amorphous silicon dioxide. Commonly, at an enzyme concentration of 1 µg recombinant silicase, 3 ng silicic acid/assay per assay are released. At higher protein concentrations (3 or 10 µg/assay) the release of silicic acid is 20 or 43 ng/assay.

3.3. Silicase-activity in *Escherichia coli*-lysate

The silicase-activity can also be determined in lysates of *E. coli* that were transformed with the SDSIA-gene of *S. domuncula* (in the following example, the short form was used;=SDSIA-s) using the "GST fusion"-system. In the experiment as shown in table 1 sponge-spicules (needles; 1 mg) were incubated at different temperatures with 1.5 ml lysate, to which 1 mM $ZnCl_2$ and 0.1 M NaCl were added. After 1, 3, 6, and 24 h the samples were denaturated by heating to 95° C. for 10 min (for inactivating the silicase), and the incubated with proteinase K (30 Units/ml) at 37° C. for 1 h. A subsequently centrifugation (5 min, 14000 rpm) followed, and the molybdenum-assay (kit of the company Merck; see above) was used for a determination of the released silicate. It was found that at 4° C. only a very small amount of silicate was released, nevertheless at room temperature (22° C.) and 56° C. up to 3.4 and 4.1 ng/ml (24 h), respectively.

A slightly lower amount of released silicate could also be determined in lysates from non-transformed *E. coli* indicating the also in bacterial cell extracts a marked silicate-decomposing activity is present.

TABLE 1

Silicase-activity in lysates of transformed (+) and non-transformed (−) *E. coli* at different temperatures of incubation. For the transformation the short form of SDSIA-gene of *S. domuncula* (= SDSIA-s) was used. The release of silicate was determined after a time of incubation of 1, 3, 6, and 24 hours.

| Temperature | Released silicate (ng/ml) | | | |
| --- | --- | --- | --- | --- |
| | 1 h | 3 h | 6 h | 24 h |
| 4° C. (−) | 0.113 | 0.124 | 0.242 | 0.303 |
| 4° C. (+) | 0.110 | 0.140 | 0.526 | 0.828 |
| 22° C. (−) | 0.197 | 0.415 | 1.467 | 2.068 |
| 22° C. (+) | 0.528 | 0.540 | 1.939 | 3.409 |
| 56° C. (−) | 0.345 | 1.009 | 1.824 | 2.447 |
| 56° C. (+) | 1.542 | 1.747 | 2.275 | 4.092 |

3.4. Silicase-activity of Commercial Carbonic Anhydrases

A silicase-activity can not only be measured in the sponge-enzyme, but surprisingly also in commercial carbonic anhydrases. Table 2 shows the release of silicate from skeletons of diatoms (silicate-scaffolds of diatoms) as well as from sand by a commercial carbonic anhydrase-preparation (from bovine erythrocytes; company Calbiochem). In the experiment, the silicate-samples were first washed twice with water and twice with ethanol and then dried. Subsequently, the samples were suspended in 50 mM Tris-HCl-buffer, pH 7.6 (1 mg/ml) and dispersed in 2 ml-Eppendorf-tubes (100 µl per reaction tube;=100 pg silicate per reaction tube). Then, 1.4 ml bovine carbonic anhydrase (10 units; company Calbiochem) in 50 mM Tris-HCl-buffer, pH 7.6 (with and without 1 mM $ZnCl_2$) were added per reaction tube. The tubes were incubated at room temperature (22° C.) by shaking for 24 h. Then, the preparations were centrifuged (14000×g, 15 min, 4° C.). The silicate-content in the supernatant was determined with the aid of the molybdenum-assay of the company Merck (see above).

TABLE 2 silicase-activity of a commercial carbonic anhydrase-preparation (company Calbiochem) with and without addition of $ZnCl_2$. The release of silicate was determined after an incubation time of 24 hours.

| | Released silicate (ng/ml) | |
| --- | --- | --- |
| | Diatoms | Sand |
| Minus $ZnCl_2$ | 0.0018 | 0.0036 |
| Plus $ZnCl_2$ | 2.0233 | 0.0359 |

3.5. Reversibility of the Silicase-activity

The silicase-reaction in principle is reversible. Thus, the reaction can also be used for the synthesis of amorphous silicon dioxide or silicones. For the silicase-mediated synthesis also alkyl or aryl substituted alkoxy compounds of silicon(IV), such as tetraalkoxysilanes, trialkoxysilanoles, dialkoxysilandioles, monoalkoxysilantrioles, alkyl or aryl trialkoxysilanes, alkyl or aryl dialkoxysilanoles or alkyl or aryl monoalkoxysilandioles can be used. In addition, mixtures of these substrates are polymerised. Therefore, also mixed polymers can be produced.

4. Ligation of the cDNA for Silicase with One or Several cDNA(S) for Other Proteins 4.1. Production of Silicase-fusion Proteins For a production of fusion proteins with the silicase a suitable expression vector (for example pQE-30-vector; Qiagen) is used. The silicase-cDNA—having e.g. a Bam HI-restriction site at its 5'-terminus and e.g. a Sal I restriction site at its 3'-terminus—is produced. The stop-codon in the silicase-cDNA is removed. For this, the PCR-technique is used, and for the amplification primers, which have the respective restriction sites, are used. The cDNA for the second protein is obtained accordingly, whereby at the 5'-terminus the same cutting site is present as at the 3'-terminus of the silicase-cDNA (Sal I in the example) and one that is different from the other is present at the 3'-terminus (e.g. a Hind III-site). If internal restriction sites are present in the respective cDNAs, alternative restriction enzymes can be used. In addition, linkers between both cDNAs can be used.

Both cDNAs are ligated according to the common method, purified and ligated into the pQE-30-vector. The ligation takes place following the histidine-tag (about 6 histidine-codons). The expression and purification of the fusion protein using, e.g. the histidine-tag being present at the recombinant protein, can be performed on respective affinity columns, e.g. a Ni-NTA-matrix (Skorokhod A, Schäcke H, Diehl-Seifert B, Steffen R, Hofmeister A, Müller W E G (1997) Cell Mol Biol 43: 509-519).

4.2. Separate Expression I (Protease-cleavage Site)

As an alternative to the method at 4.1. a protease-cleavage site (such as, for example, an enterokinase-site) can be cloned between the cDNA for the silicase and the cDNA for an additional protein. In this case a codon for a novel start-methionine can be inserted in front of the encoding region of the gene for the additional protein. Following expression and purification the fusion protein is proteolytically cleaved. Now, both proteins are present separately.

4.3. Separate Expression II (Cassette-expression)

As an alternative, both proteins can be expressed separately on one construct. For this, in an expression-vector the silicase-gene is following the his-tag. At the end of the silicase-cDNA, a stop-codon is inserted. A ribosome-binding site with a codon for a start-methionine is cloned between the cDNA for the silicase and the cDNA for the additional protein. Again, a his-tag is positioned in front of the cDNA for the additional protein. Also this gene is provided with a stop-codon.

The his-tags can be deleted, if the proteins are used fort he functional analysis in the respective host cells.

4.4. Extensions

For the expression described at 4.1 to 4.3 bacterial as well as eukaryotic cells can be used.

The expression described at 4.1 to 4.3 can also be used for three and more open reading frames.

5. The Model System for the Synthesis/the Degradation of Biogenic Silicon Dioxide: Primmorphs

5. 1. Primmorphs

A patent application was filed for the Primmorph-system (DE 19824384. Herstellung von Primmorphe aus dissoziierten Zellen von Schwämmen, Korallen und weiteren Invertebraten: Verfahren zur Kultivierung von Zellen von Schwämmen und weiteren Invertebraten zur Produktion und Detektion von bioaktiven Substanzen, zur Detektion von Umweltgiften und zur Kultivierung dieser Tiere in Aquarien und im Freiland. Inventors and applicants: Müller W E G, Brümmer F).

Primmorphs are aggregates that consist out of proliferating and differentiating cells (Müller W E G, Wiens M, Batel R, Steffen R, Borojevic R, Custodio M R (1999) Establishment of a primary cell culture from a sponge: Primmorphs from *Suberites domucula*. Marine Ecol Progr Ser 178 : 205-219). Primmorphs are formed from sponge single cells that are obtained from sponge tissue after dissociation in $Ca^{2+}$ and $Mg^{2+}$ free, EDTA containing artificial seawater.

Aggregates are formed from the sponge single cells after transfer into $Ca^{2+}$ and $Mg^{2+}$-containing seawater that after 3 days reach a size of 1 mm, and after 5 days Primmorphs with a diameter of about 5 mm.

The Primmorphs are surrounded by epithelium-like cells, the pinacocytes. The cells within the Primmorphs are primarily spherical cells, in addition, amoebocytes and archaeocytes are present.

5.2. Effect of Silicon on the Formation of Spicules

The Primmorph-system of sponges, e.g. *S. domuncula*, can be used fort he examination of the formation or dissolution of spicules.

For this, Primmorphs are cultivated for 8 days in seawater that was supplemented with 30 uM Fe(+++) (added as citrate) and 10% RPM11640-medium. The silicon-concentration in seawater/medium is 5 μM. After 8 days the Primmorphs are either further incubated in this medium or transferred in a medium containing 60 μM silicon (the silicon-concentration being optimal for the formation of spicules; added as Na-hexafluorosilicate), and cultivated for 1 or 3 days.

Primmorphs that were cultivated without the addition of silicon primarily show a round, spherical shape.

FIG. 6A shows that most of the Primmorphs after additional 3-day culture in the presence of 60 μM silicon become ovally shaped. In the presence of silicon, the Primmorphs start with the formation of spicules. Partially, the synthesis of long (>100 um) spicules can be observed (FIG. 6B), nevertheless, more often smaller spicules (30 um) are found (FIG. 6D). In the absence of silicon, no spicules are present (FIG. 6C).

5.3. Silicon-responsive Genes

In Primmorphs of *S. domuncula* the expression of the silicase-gene is up-regulated in the presence of silicon. In parallel also the expression of the following genes is increased: silicatein, collagen, myotrophin and isocitrate-dehydrogenase.

The expression of the silicase-gene can be determined by Northern-blotting using methods that are state of the art were, for example, used for the determination of the expression of silicatein and collagen (Krasko A, Batel R, Schröder H C, Müller I M, Müller W E G (2000) Expression of silicatein and collagen genes in the marine sponge *Suberites domucula* is controlled by silicate and myotrophin. Europ J Biochem 267: 4878-4887).

In the experiment shown in FIG. 7 the Primmorphs either maintained untreated or were incubated with 60 μM silicon for 1 to 3 days. Then, the RNA was extracted. An amount of each 5 μg total-RNA was electrophoretically separated on a 1% formaldehyde/agarose-gel, blottet onto a Hybond-N+ Nylon-membrane in accordance with the instructions of the manufacturer (Amersham). The hybridisation was done with 400 to 600 bp sized segments of the following probes: SDSIA (encodes for silicase), SDSILICA (encodes silicatein), and SDIDH (encodes for the α-subunit of the isocitrate-dehydrogenase). The probes were labelled with the PCR-DIG-probe-synthesis kit in accordance with the instructions of the manufacturer (Roche). After washing the DIG-labelled nucleic acid was detected with anti-DIG Fab fragments (conjugated with alkaline phosphatase; dilution: 1:10000), and visualized with the aid of the chemoluminescence technique using CDP (Roche), the chemoluminescence-substrate of the alkaline phosphatase.

FIG. 7 shows the Northern-blots that were obtained. It can be seen that the genes for the silicase and silicatein are strongly up-regulated in response to higher silicon concentrations. Furthermore also the gene for isocitrate-dehydrogenase (encodes for an enzyme being involved in the citric acid cycle) are up-regulated indicating that the formation of amorphous silicon dioxide requires an increased metabolic rate of the cells.

6. Mode of Action of the Silicase

The finding obtained by the sequence comparisons, that the silicase is a member of the family of carbonic anhydrases (carbonate-hydrolase; EC 4.2. 1.1), was surprising.

These enzymes catalyse the reversible hydration of carbon dioxide (FIG. 8A). Carbon dioxide is converted into $HCO_3^-$ and $H^+$ by the carbonic anhydrase.

The silicase indeed also exhibits a carbonic anhydrase-activity, as could be shown with a colorimetric assay (Armstrong J M, Myers D V, Verpoorte J A, Edsall J T (1966) Purification and properties of human erythrocyte carbonic anhydrase. J Biol Chem 241: 5137-5149). Accordingly, it is possible that the silicase causes a change of the pH because of the conversion of $CO_2$ into $HCO_3^-$ (FIG. 8A). This allows for an etching of lime substrates, but not of silicon dioxide-materials, whose solubility increases with increasing but not lowering pH.

It is known that some species of sponges such as species of the genus *Cliona* are able to dissolve calcium carbonate and to burrow holes into calcite/aragonite-substrates (Rützler K, Rieger G (1973) Sponge burrowing: fine structure of *Cliona lampa* penetrating calcareous substrata. Mar Biol 21: 144-162).

Nevertheless the silicase-activity of the enzyme was unknown and surprising.

It is known that three histidine residues are involved in the mode of action (carbonic anhydrase-activity) of the carbonic anhydrase that bind to a divalent zinc ion; accordingly, the following mode of action can be formulated for the silicase-activity (FIG. 8B). In the silicase of *S. domuncula* the histidine residues are found in the derived polypeptide at the amino acid positions $aa_{181}$, $aa_{183}$ and $aa_{206}$ (FIG. 3A). In water (Lewis-base) a hydroxide anion is formed that is bound to the $Zn^{2+}$ (Lewis-acid). This performs a nucleophilic attack at one of the silicon atoms that are linked one with the other by oxygen atoms (FIG. 8B). In the next step the zinc-complex binds to the silicon atom by cleaving of the oxygen bond. Under consumption of $H_2O$ finally a free silicic acid is released the initial zinc(II)-bound hydroxide anion is formed again.

7. Uses of the Silicase and Silicase-fusion Proteins

For the recombinant silicase, the silicase as purified from different sources, and the silicase-fusion proteins a series of different industrial and technical uses are found, namely:

1.) Use for the surface modification of biomaterials (improvement of the biocompatibility). Surface-modified biomaterials find use amongst others for influencing of cellular adhesion and growth, for modifying the blood compatibility or for controlling the protein-adsorption (e.g. reduction of the adsorption of contact lenses). A literature compendium can be found in: Ratner B D et al (eds.) Biomaterials Science—An Introduction to Materials in Medicine. Academic Press, San Diego, 1996. One problem consists in the fact that the conditions used for the production of these modifications often have a deleterious (destructive) effect on the used biomaterials. A "mild" and biomaterial protective method compared to the physical/chemical methods as used is represented by a modification of the surfaces that is solely based on biochemical/enzymatic reactions that becomes possible with the aid of the method according to the invention (silicase-mediated enzymatic degradation and—as reversible reaction—enzymatic synthesis of $SiO_2$ or siloxane containing of surfaces with the aid of the recombinant/purified silicase). In particular, also a use of the recombinant or silicase as purified from natural sources in the production of surface modifications (during coating) of silicone-materials, such as silicone breast implants, endo-prostheses or metal-implants (improvement of the connection between bones and metal-implants, biologization of the metal-implants) as well as contact/plastic lenses is resulting. Further uses relate to the coating of collagen, that is used as bone replacement material, and of collagen-fleece that are, e.g., used for the "tissue engineering".

Here, the goal is the increase of stability and the porosity as well as die improvement of the resorbability.

2.) Use for the production of novel biomaterials such as bone replacement materials or dental replacement materials by a co-synthesis of poly(silicates), silicones and mixed polymers.

3.) Use for the surface modification (treatment of contact-zones) of (silicon)-semi conductors or silicon-chips.

4.) Use for the modification or for the synthesis of nanostructures from amorphous silicon dioxide. By means of the recombinant silicase, the recombinant silicase-fusion proteins or the purified silicase it becomes possible to modify or to synthesize specific two- and three dimensional structures from amorphous silicon dioxide in the nanoscale. The structures as formed can be employed in the nanotechnology.

5.) Use for the surface modification of silicon-containing precious stones and semi-precious stones. Agate, jasper, and onyx, amongst others, belong to the amorphous or fine crystalline modifications of the $SiO_2$. Due to the possibility to modify the surface of these minerals with the aid of the silicase under controlled conditions, the use of the methods according to the invention in the production or processing of these precious stones/semi-precious stones is resulting. Here, also the possibility to selectively introduce foreign molecules/atoms is resulting.

6. Use in the modification or synthesis von silicon-organic compounds including sila-pharmaceutics. For an overview about the production of silicon-organic compounds as a basis for so called sila-pharmaceutics (pharmaceutics wherein C is replaced by Si), see: Chem. unserer Zeit 14,197-207 (1980), as well as: Bioactive Organo-Silicon Compounds (Topics Curr. Chem. 84), Berlin, Springer 1979). By means of the method according to the invention novel, enzymatic pathways for the modification or synthesis of such compounds are possible.

8. Uses of the Silicase and Silicase-fusion Proteins for the Prevention and Therapy of Solicosis (Quartz Dust-lung Disease)

8.1. Silicosis

Crystalline silicic acid (silicon dioxide), in the form von quartz, tridymite or cristobalite, is most likely one of the most important hazardous compound during work. The severity of the adverse effect on the health and the diversity of the possible sources of exposure are known for a long time. Due to the widespread occurrence of crystalline silicon dioxide in the crust of the earth and the common use of materials containing it, in particular workers in a variety of different industrial businesses are exposed to crystalline silicon dioxide. It can be assumed that in agriculture, in mining, in the glass and glass-fiber industry, as well as in the production of cement, in the production of ceramics, in casting houses, in the production of colors, soaps and cosmetics or in the dental manufacture/repair millions of employees are regularly exposed to crystalline silicon dioxide. According to the "American Thoracic Society" silicon dioxide word-wide is one of the major causes of lung disease. Thus, a large need exists fort he development of strategies for the prevention and therapy.

It is known that inhaled crystalline silicon dioxide causes lung fibrosis (silicosis) and lung cancer. The silicosis is a malign pneumoconiosis that is caused by an accumulation of silicon dioxide-particles in the tissue of the lung, is characterized by the occurrence of silicotic nodules. A rational therapy of this disease leading to a severe disabling does not exists.

A major reason for the toxicity of dust-like crystalline silicon dioxide can be found in the fact that the lung is not able to eliminate the inhaled dust particles. The silicon dioxide-particles remaining in the lung tissue lead to inflammatory reactions and to the formation of cell-toxic cytokines, proteases, and reactive oxygen radicals. A continuation of these phenomena results in a proliferation of connective tissue results with an increased formation of collagen in the lung, leading to the generation of pneumoconiosis.

In general, silicosis is developing very slowly over the course of decades. It is a progressive disease that can not be cured. It is first apparent by dyspnoea, dry cough, and sharp pain in the chest. A congestion of the heart and an obstruction of respiration and circulation finally lead to death. The average period of time between the exposition to dust and the occurrence of the silicosis is found at about 20 years. A dangerous complication of the silicosis is the silico-tuberculosis The mechanism leading to the development of lung cancer by crystalline silicon dioxide is only understood to a very limited extent.

Silicosis is the most common dust-lung disease amongst the industrial diseases.

The mean total costs for a silicosis-patient are in the order of about 130.000 Euro.

8.2. Therapeutics/Protective Agent in Silicosis

The silicase that is involved in the dissolution of biogenic silicon dioxide can be used as therapeutic/protective agent for the treatment of silicosis.

The silicase is not only able to dissolve amorphous but also crystalline silicon dioxide (quartz crystals).

The silicase therefore exhibits the properties as necessary, in order to eliminate silicon dioxide from the lung and/or to modulate the progression of this lung disease.

Different methods fort he administration of the recombinant enzyme can be taken into account: a) as enzyme preparation, b) packaged in liposomes, c) associated with microspheres or d) adenovirus-mediated gene transfer.

Microspheres as carrier-systems for the recombinant silicase for the treatment of silicosis (dissolution of $SiO_2$) e.g. can be prepared from sponge-collagen in analogy to calf-collagen-microspheres (Rössler et al., Pharmazie 49 (1994) 175-179). Die sponge-collagen-microparticles are loaded by adsorption of the recombinant protein (silicase), as described (Rössler et al., J. Microencapsulation 12 (1995) 49-57; Berthold et al., Eur. J. Pharm. Biopharm. 45 (1998) 23-29). The advantages of collagen are its bio-degradability as well as its low toxicity and immunogenicity. As further "Delivery"-systems, amongst other, liposomes with the encased recombinant enzyme as well as lipid-nanoparticle can be taken into account (Jenning et al., Eur. J. Pharm. Biopharm. 49 (2000) 211-218).

8.3. Modification of the Properties of Cells by Transfection With a Silicase Gene/cDNA-containing Plasmid Through a transfection of cells with a silicase gene/cDNA-containing plasmid, their properties can be modified, allowing for, amongst others, a use in the production of bone replacement materials or a gene therapy (e.g. in silicosis).

EXPLANATIONS TO THE FIGURES

In the following, the explanatory legends for the accompanying drawings and the sequence protocol are given. It shows:

SEQ ID No. 1: The amino acid sequence of the silicase according to the invention from S. domuncula (SIA SUBDO).

SEQ ID No. 2: The nucleic acid sequence of the cDNA of the silicase according to the invention from S. domuncula.

FIG. 1: Identification of transcripts in Primmorphs that were up-regulated after incubation in 60 μM silicon for 1 or 3 days, with the aid of the technique of the differential display. The Primmorphs were either maintained at the normal silicon-concentration of 5 μM (lane a) or were incubated in the presence of 60 μM silicon (lane b and c). The RNA was extracted and used for the analysis. For amplification of the transcripts two different random primer (1 and 2) were used. Those transcripts are marked (>) which only occurred at higher silicon-concentration (lane b and c) and were analyzed.

FIGS. 2A and 2B: FIG. 2A: Amino acid sequence derived from the nucleotide sequence of the open reading frame (coding region) of the S. domuncula silicase-cDNA (SIA_SUBDO). FIG. 2B: Nucleotide sequence of the S. domuncula Silicase-cDNA (SIA_SUBDO). The amino acid sequence derived from the nucleotide sequence of the open reading frame is given below the nucleotide sequence.

FIGS. 3A and 3B: FIG. 3A: (A) Alignment of the S. domuncula silicase (SIA_SUBDO) with the human carbonic anhydrase 11 (carbonate dehydratase II) (CAH2_HUMAN; P00918). The carbonic anhydrase domain is framed (|=e-CAdom=|). The characteristic amino acids that form the eukaryotic-type-carbonic anhydrase-signature, are marked (▲: found in both sequences; ■: present only in the carbonic anhydrase but not in the silicase). The additional symbols (+) indicate those residues, that form the hydrogen-network of the active center. The three zinc-binding histidine-residues are marked (Z). Similar amino acid residues between both sequences are highlighted. The borders of the long (~rec~ to ~rec~) as well as the short recombinant silicase (~rec-s~ to ~rec~) are marked and underlined twice. FIG. 3B: phylogenetic tree, constructed with the sponge-silicase and following related enzymes: human carbonanhydrase I (carbonate dehydratase I) (CAH1_HUMAN; P00915), II (CAH2~HUMAN), III (CAH3_HUMAN; P07451), IV (CAH4_HUMAN; P22748), VI (CAH6_HUMAN; P23280), VII (CAH7_HUMAN; P43166), VIII (CAH8_HUMAN; P35219), IX (CAH9_HUMAN; Q16790), X (CAHA HUMAN; Q9NS85), VA (CAH5_HUMAN; P35218), VB (CA5B_HUMAN; Q9Y2D0), XII (CAHC_HUMAN; 043570), XIV (CAHE_HUMAN; Q9ULX7), carbonic anhydrase of Caenorhabditis elegans (CAH_CAEEL; Nu-510674.1), carbonic anhydrase of Drosophila melanogaster (CAH1_DROME; NP523561.1), carbonic anhydrase of the plants Arabidopsis thaliana (CAH-I_ARATH; NP_196038.1) and Chlamydomonas reinhardtii (carbonate dehydratase 1) (CAH1CHLRE ; P20507) as well as bacterial carbonic anhydrases from Neisseria gonorrhoeae (CAH_NEIGO; Q50940), Klebsiella pneumoniae (CAH_KLEPN; 052535) and the cyanobacteria Nostoc sp. PCC 7120 (CAHANASP; P94170). The latter sequence were used as outgroup. The measure bars indicate an evolutionary distance of 0.1 amino acid-substitutions per position in the sequence. The phylogenetic tree was constructed by means of "Neighbor-Joining" ("Neighbor" program: Felsenstein, J. (1993). PHYLIP, ver. 3.5. University of Washington, Seattle).

FIG. 4: Production of the recombinant silicase. The recombinant S. domuncula Silicase (rSIA_SUBDO) was produced as GST-fusion protein. The long as well as the short SDSIA were cloned in a pGEX-4T-2-plasmid that contained the glutathione-S-transferase (GST)-gene. The fusion proteins were isolated either without prior induction with IPTG (-IPTG) or after incubation with IPTG (+IPTG) for 4 or 6 hours, subsequently cleaved, purified and subsequently subjected to the Na-DodSO$_4$-PAGE. The gel was stained with Coomassie Brillant Blue. The purified long form rSIA_SUBDO-I with a size of 43 kDa as well as the short form ($M_r$ 32 kDa) of the silicase were obtained.

FIG. 5: Determination of the enzymatic activity of the silicase in the carbonic anhydrase and in the silicase assay. The recombinant silicase was added to the reaction mixtures, in concentrations between 1 and 10 μg per assay (0.56 μl). For the determination of the carbonic anhydrase-activity (■) p-nitrophenyl acetate was used as a substrate. The released p-nitrophenol was measured at a wavelength von 348 nm. The activity of the silicase (•) was determined with the use of *S. domuncula* spicules. The released silicic acid as formed by depolymerisation (decomposition) of amorphous silicon dioxide was determined with the aid of the "Silicon Test" colorimetric reaction.

FIGS. 6A-6D Effect von silicon on the formation of spicules in Primmorphs. For the formation of the Primmorphs dissociated cells of the marine sponge *S. domuncula* were incubated in sea water, supplemented with 10% RPM 11640-Medium and 30 µM Fe(+++). The Primmorphs were then transferred for 3 days into a medium (RPMI 1640, Fe(+++)) that was enriched with 60 µM silicon. (A) The Primmorphs were incubated in medium plus silicon magnification: ×6. (B) In some cases the Primmorphs started with the synthesis of spicules (sp). magnification: ×10. For the semi-quantitative determination, the Primmorphs were pressed between two cover slides (C and D). (C) Primmorphs that were incubated in the absence of silicon inkubiert were nearly completely without spicules, whereas those that were cultivated in the presence of silicon contained newly formed spicules (>); (D); magnification: ×200

FIG. 7: Expression of the silicase, the silicatein, and the isocitrate-dehydrogenase, determined by Northern-Blotting. The RNA was extracted from Primmorphs that were incubated for 1 to 3 days in the absence of additional silicon (−Si) or in the presence of 60 µM silicon (+Si). 5 µg of the total RNA were electrophoretically separated, blotted onto Nylon membranes and hybridized with the following probes: SDSIA (silicase), SDSILICA (silicatein), and SDIDH (α-subunit of the isocitrate-dehydrogenase). The sizes of the transcripts are given.

FIGS. 8A and 8B: Enzymatic reactions as mediates by the silicase (carbonic anhydrase) of *S. domuncula*. In FIG. 8A the conversion of $CO_2$ into $HCO_3^-$ is shown. In FIG. 8B, the reaction of the silicase is shown. The silicase binds one zinc atom with its three histidine-residues. The zinc ion, a Lewis-acid, binds a hydroxide-anion that is derived from water, a Lewis-base. The silicase/zinc-complex undertakes a nucleophilic attack auf a silicon atom between the oxygen bonds. Thereby, the hydrolysis of the polymeric silicon dioxide is achieved, which first—with one of both product halves—maintains bound to the enzyme. Upon further consumption of $H_2O$, the product is released until finally free silicic acid is left after several cycles.

Figures 9A, 9B:
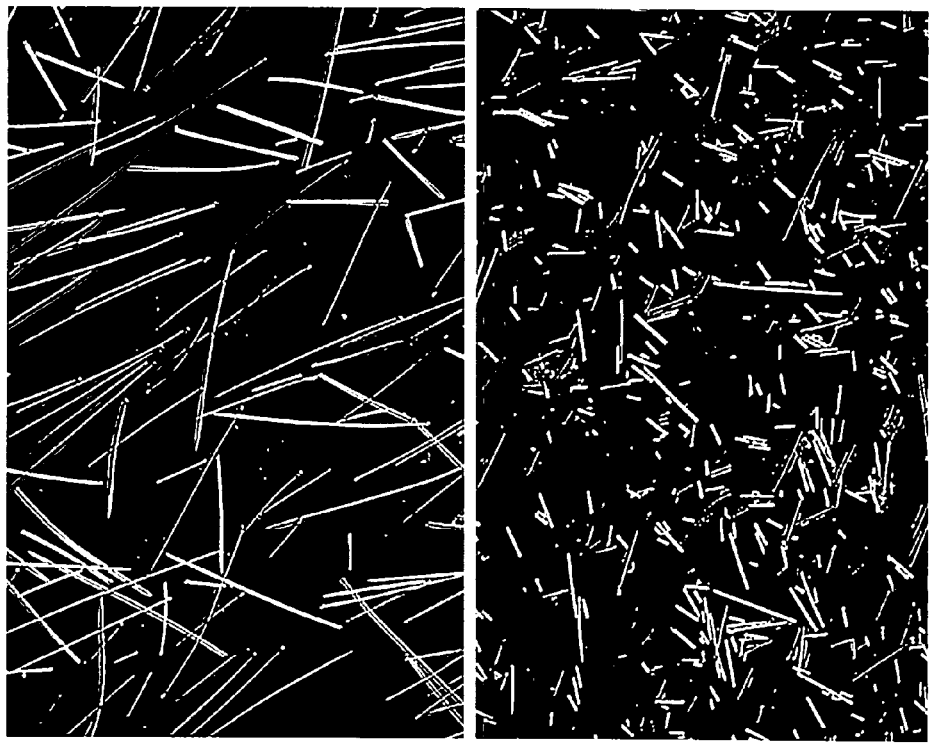

FIGS. 9A and 9B: FIG. 9A: Spicules (needles) of *Suberites domuncula* after 6 hour incubation in the absence of silicase. FIG. 9B: Spicules of *Suberites domuncula* after 6 hour incubation in the presence of silicase. The incubation took place under the conditions as described in table 2.

The invention claimed is:

1. A method for the synthesis of amorphous silicone dioxide (condensation products of the silicic acid, silicates), silicones or other silicon (IV)- or metal (IV)-compounds or mixed polymers of these compounds comprising contacting a silicon substrate (or substrates) with a polypeptide or a metal complex of a polypeptide comprising a carbonic anhydrase domain that exhibits the sequence of SEQ ID NO: 1.

2. The method according to claim 1 for the synthesis of amorphous silicone dioxide (condensation products of the silicic acid, silicates), silicones or other silicon (IV)- or metal (IV)-compounds or mixed polymers of these compounds comprising contacting a substrate, wherein the substrate(s) is selected from the group consisting of silicic acids, monoalkoxysilantrioles, dialkoxysilandioles, trialkoxysilanoles, tetraalkoxysilanes, alkyl- or aryl-silantrioles, alkyl- or aryl-monoalkoxysilandioles, alkyl- or aryl-dialkoxysilanoles, alkyl- or aryl-trialkoxysilanes or other metal(IV)-compounds.

3. The method according to claim 2, wherein mixed polymers having a defined composition are produced by using defined mixtures of the substrate compounds.

4. The method according to claim 1, wherein the synthesized silica product(s) comprise defined two- and three-dimensional structures.

* * * * *

UNITED STATES PATENT AND TRADEMARK OFFICE
CERTIFICATE OF CORRECTION

PATENT NO. : 7,229,807 B2
APPLICATION NO. : 10/530240
DATED : June 12, 2007
INVENTOR(S) : Werner E. G. Müller, Heinz Schröder and Anatoli Krasko It is certified that error appears in the above-identified patent and that said Letters Patent is hereby corrected as shown below:

Column 1,
Line 2, "Silase" should read --Silicase--.

Signed and Sealed this

Eighteenth Day of March, 2008

JON W. DUDAS
*Director of the United States Patent and Trademark Office*